United States Patent [19]
Tripp et al.

[11] Patent Number: 5,849,537
[45] Date of Patent: Dec. 15, 1998

[54] METHOD OF EXPRESSING ANTIFREEZE PROTEINS IN YEAST

[75] Inventors: Matthew Tripp, Nashotah; Lance Lusk, Milwaukee; Thomas Rhodes, Cedarburg; Nick Huige, Brookfield; Edward Kot, Delafield; Etzer Chicoye; Michael C. Barney, both of Wauwatosa; Patricia A. Bower, Milwaukee; Charles L. Cronan, Shorewood, all of Wis.

[73] Assignee: Miller Brewing Company, Milwaukee, Wis.

[21] Appl. No.: 180,524

[22] Filed: Jan. 12, 1994

Related U.S. Application Data

[63] Continuation of Ser. No. 917,216, Jul. 20, 1992, abandoned, which is a continuation-in-part of Ser. No. 486,333, Feb. 28, 1990, abandoned, which is a continuation-in-part of Ser. No. 409,217, Sep. 19, 1989, abandoned.

[51] Int. Cl.$^6$ .......................... C12P 21/02; C12N 15/81; C12N 1/19
[52] U.S. Cl. ................ 435/69.7; 435/172.3; 435/254.21; 435/320.1; 536/23.4; 536/23.5
[58] Field of Search ............................. 435/254.2, 320.1, 435/172.3, 69.1, 69.7, 172.1, 240.2, 254.21, 254.1; 536/23.4, 23.5

[56] References Cited

U.S. PATENT DOCUMENTS

| | | | |
|---|---|---|---|
| 4,769,328 | 9/1988 | Murray et al. | 435/69.1 |
| 4,839,283 | 6/1989 | Kawasaki et al. | 435/69.2 |
| 5,118,792 | 6/1992 | Warren et al. | 530/350 |

FOREIGN PATENT DOCUMENTS

| | | |
|---|---|---|
| 00876 | 9/1988 | WIPO . |
| 88/07076 | 9/1988 | WIPO . |

OTHER PUBLICATIONS

Gronlic et al J Biol. Chem. 259:14960 (1984).
Pesole et al. Nuc Acid Res vol. 16: 1715 (1988).
Davies et al. PNAS 79:335 (1982).
Britz (1987) Austral. J Biotech. 1(3), 29–40.
Ginsberg et al. (1979) J. Clin. Endrocrin Metab. 48(1), 43–49.
Scopes (1982) "Protein Purification", p. 183 Springer/Verlag, N.Y.
Brake et al. (1984) PNAS vol. 81: 4642–4646.
Gourlie et al. (1984) J. Biol. Chem. 259:14960.
Pesole et al. (1988) Nuc. Acid Res: 1715.
Davies et al. (1982) PNAS 79:335.
Peterson, Ivers, Science News, "A Biological Antifreeze" vol. 130, pp. 330–332. (1986).

*Primary Examiner*—David Guzo
*Attorney, Agent, or Firm*—Quarles & Brady

[57] ABSTRACT

Yeast is genetically engineered by transformation with an expression vector containing a natural yeast secretion signal sequence combined appropriately with a chemically synthesized gene encoding antifreeze protein resulting in the expression, proper processing, and secretion of antifreeze protein which is heterologous to yeast in recoverable amounts. Disclosed are DNA sequences comprising structural genes encoding peptides having amino acid sequences with the biochemical or physiochemical properties of antifreeze protein and a method of combining the antifreeze protein gene sequences with appropriate expression vectors.

9 Claims, 11 Drawing Sheets

FIG. I

```
                10        20        30        40        50        60
       CGACAGTAAATTTTGCCGAATTTAATAGCTTCTACTGAAAAACAGTGGACCATGTGAAAA 70        80        90       100       110       120
       GATGCATCTCATTTATCAAACACATAATATTCAAGTGAGCCTTACTTCAATTGTATTGAA 130       140       150       160       170       180
       GTGCAAGAAAACCAAAAAGCAACAACAGGTTTTGGATAAGTACATATATAAGAGGGCCTT 190       200       210       220       230       240
       TTGTTCCCATCAAAAATGTTACTGTTCTTACGATTCATTTACGATTCAAGAATAGTTCAA 250       260       270       280       290       300
       ACAASAAGATTACAAACTATCAATTTCATACACAATATAAACGATTAAAAGAATGAGATT
                                                           MetArgPh 310       320       330       340       350       360
       TCCTTCAATTTTTACTGCAGTTTTATTCGCAGCATCCTCCGCATTAGCTGCTCCAGTCAA
       eProSerIlePheThrAlaValLeuPheAlaAlaSerSerAlaLeuAlaAlaProValAs 370       380       390       400       410       420
       CACTACAACAGAAGATGAAACGGCACAAATTCCGGCTGAAGCTGTCATCGGTTACTTAGA
       nThrThrThROluAspGluThrAlaGlnIleProAlaGluAlaValIleGlyTyrLeuAs 430       440       450       460       470       480
       TTTAGAAGGGGATTTCGATGTTGCTGTTTTGCCATTTTCCAACAGCACAAATAACGGGTT
       pLeuGluGlyAspPheAspValAlaValLeuProPheSerAsnSerThrAsnAsnGlyLe 490       500       510       520       530       540
       ATTGTTTATAAATACTACTATTGCCAGCATTGCTGCTAAAGAAGAAGGGGTATCTTTGGA
       uLeuPheIleAsnThrThrIleAlaSerIleAlaAlaLysGluGluGlyValSerLeuAs 550       560       570       580       590       600
       TAAAAGAGAGGCTGAAGCTTCTTTGGATAAAAGAGACACTGCTTCTGACGCTGCCGCTGC
       pLysArgGluAlaGluAlaSerLeuAspLysArgAspThrAlaSerAspAlaAlaAlaAl 610       620       630       640       650       660
       TGCTGCTTTGACTGCCGCTAACGCTAAGGCCGCTGCTGAATTGACTGCTGCTAACGCTGC
       aAlaAlaLeuThrAlaAlaAsnAlaLysAlaAlaAlaGluLeuThrAlaAlaAsnAlaAl 670       680       690       700
       CGCCGCCGCCGCTGCCACTGCTAGATAAGGATCCGAATTCGTCGAC
       aAlaAlaAlaAlaAlaThrAlaArg
```

AFP GENE

HIND3

```
5' AGCT TCT TTG GAT AAA AGA GAC ACT GCT TCT GAC GCT GCC GCT GCT GCT GCT GCT
3'      AGA AAC CTA TTT TCT CTG TGA CGA AGA CTG CGA CGG CGA CGA CGA CGA CGA
    ALA SER LEU ASP LYS ARG ASP THR ALA SER ASP ALA ALA ALA ALA ALA ALA
    -6  -5  -4  -3  -2  -1   1   2   3   4   5   6   7   8   9  10  11
```

```
5' TTG ACT GCC GCT AAC GCT AAG GCC GCT GCT GAA TTG ACT GCT GCT AAC GCT
3' AAC TGA CGG CGA TTG CGA TTC CGG CGA CGA CTT AAC TGA CGA CGA TTG CGA
   LEU THR ALA ALA ASN ALA LYS ALA ALA ALA GLU LEU THR ALA ALA ASN ALA
   12  13  14  15  16  17  18  19  20  21  22  23  24  25  26  27  28
```

```
5' GCC GCC GCC GCT GCC GCT ACT GTT AGA TAA GGATCC  GAATTC G      3'
3' CGG CGG CGG CGA CGG CGA TGA CAA TCT ATT CCTAGG  CTTAAG CAGCT  5'
   ALA ALA ALA ALA ALA ALA THR VAL ARG STP BAMH1  EcoR1  SAL1
   29  30  31  32  33  34  35  36  37
```

FIG. 3

FRAGMENT 1

1    5' AGCT TCT TTG GAT AAA AGA GAC ACT GCT TCT GAC GCT GCC GCT GCT 46

47   5' GCT GCT TTG ACT GCC GCT AAC GC 3'                              69

FRAGMENT 2

70   5' T AAG GCC GCT GCT GAA TTG ACT GCT GCT AAC GCT GCC GCC         112

113  GCC GCT GCC ACT GCT AGA TAA GGATCC GAATTC G 3'                   146

FRAGMENT 3

1    3' AGA AAC CTA TTT TCT CTG TGA CGA AGA CTG CGA CGG CGA CGA        42

43   3' CGA CGA AAC TGA CGG CGA TTG CGA TT 5'                          69

FRAGMENT 4

70   3' C CGG CGA CGA CTT AAC TGA CGA CGA TTG CGA CGG CGG CGG         112

113  3' CGA CGG TGA CGA TCT ATT CCTAGG CTTAAG CAGCT 5'                146

FIG. 4

```
GCACAACACTGGGGAGTGTTGTACCAATCTGCTC

AGATTGGTCGACAGTCAAGGCGATGACCCAGGCTCCAGTTACTATAAAACAGATTCACATT
                                             +1                40

GACCTGGATATTCACCACATCTTCATTTTGTAGTGAACCAGTGCTCCCTACAAGTTCTCA
              60                                              100

MetAlaLeuSerLeuPheThrValGlyGlnLeuIlePheLeuPheTrpThrMetArg
AAATGGCTCTCTCTCACTTTTCACTGTCGGACAATTGATTTCTTATTTTGGACAATGAGgt
                         120                                  160 acgtgaacactcactttgttttcttctatgaatctggtttactgtaaatatccttggaagg
                         180                                  220 aaggaaggatatctgcattatccccgagggggccatttgttttacagccagcggtgaaaga
```

FIG. 5A

```
10  tgaagatcttcatccgtgttcatctgtgttgaccctgattaacacaagatggtcacatgga
                 240                                          280 ccatctttattacataatgtttcatcagcacttcctgtttcagcccgaaacttaaaga
               300                                         340

15  ggcctcatggaaacttcctgatgatctggtgacacctgctgtgttgaaggaaacagagttt
                 360                                          400
                                                                    420 gagaggcggaagaaaaattatttttagtttgaatgaagaagctgtcatttgattcatgt
               420                                         460 tgggggggggggggtcatcacacacagatattgataactgtcatcactgagtttggtga
               480                                         520

20  aagtgacggaccagtaaatgtttgatgatatatattatcataattatataataatacc
                 540                                          580
```

FIG.5B

```
                    IleThrGluAlaArgProAspProAlaAlaLysAlaAlaProAla
attaatctctgcagAATCACTGAAGCCAGACCCGACCCCGCAGCCAAAGCCGCCCCAGCA
600                             640

AlaAlaAlaAlaProAlaAlaAlaAlaAlaProAspThrAlaSerAspAlaAlaAlaAla
GCAGCTGCCGCCCCTGCCGCAGCCGCCCCAGACACCGCCTCTGACGCCGCTGCAGCC
    660                             700

AlaLeuThrAlaAlaAlaAsnAlaAlaLysAlaAlaAlaAlaGluLeuThrAlaAlaAsnAlaAlaAla
GCCCTTACCGCCGCCAACGCCAAAGCCGCCGCCGAACTCACTGCCGCCAACGCCGCCGCC
        720                             760

AlaAlaAlaAlaThrAlaArgGly
GCCGCAGCAGCCACCGCCAGAGGTTAAGGATCGTGGTCGTCTTGATGTGGGATCATGTGA
10              780                     820
```

FIG. 5C

15 ACATCTGAGGAGCGAGATGTTACCAATCTGCTGAATAAACCTGAGAAGCTGATTGTTAAA
                                                    880
AACCAAGTGTCCTGTTCATTTCATCTCTGAAAGTCCGTCACAGTTTCTGTAGATCATGTA
                                                    940
GACTCCAGGAAGTGATGCCATTGTGCTGTTGAACCTGCAG
     960

FIG. 5D

METHOD OF EXPRESSING ANTIFREEZE PROTEINS IN YEAST

RELATED CASES

This application is a continuation of application Ser. No. 07/917,216, filed Jul. 20, 1992, now abandoned which is a continuation-in-part of U.S. patent application 07/486,333, filed Feb. 28, 1990, now abandoned which is a continuation-in-part of U.S. patent application Ser. No. 07/409,217, filed Sep. 19, 1989 now abandoned. These patent applications are hereby incorporated by reference.

FIELD OF THE INVENTION

The present invention relates generally to the manipulation of genetic materials and particularly to the manufacture and use of specific DNA sequences useful in recombinant procedures to secure the production of peptides having one or more of the biochemical and physiochemical properties of antifreeze proteins. More particularly, the present invention relates to a method for expressing antifreeze proteins in yeast.

BACKGROUND OF THE INVENTION

Antifreeze proteins (AFP) are a family of peptides naturally found in fish inhabiting extremely cold polar marine waters and are believed to protect them from freezing While ordinary fish would freeze solid in the 28.5° F. to 32° F. polar oceans, fish containing AFP stay fluid and flexible in these supercooled waters. The mechanism of action of AFP is still largely unknown. Aqueous solutions containing AFP possess many unusual freezing properties. For example, AFP lowers the freezing point of a solution in a non-colligative manner resulting in little or no effect on the melting point. Hence, an AFP solution may have a freezing point of −2° C., but a melting point of −1° C. In contrast, salts typically depress the freezing point and melting point equally. Along the same lines, AFP lowers the temperature at which an ice crystal will grow but does not lower the melting point. It is this property of AFP that may be the most important in regards to protecting the fish because it is the physical damage caused by ice crystal growth through membranes which is a major cause of freezing injury and death. It has been proposed that the activity of AFP is the result of its ability to inhibit ice growth through adsorption to the ice surface (Raymond, J. A. & DeVries, A. L. 1977 PNAS U.S.A. 74, 2589–2593). For example, ice normally grows in directions perpendicular to the c axis (Fletcher, N. H. 1970 "The Chemical Physics of Ice", Cambridge Univ. Press, Cambridge); AFP inhibits growth in these directions (Raymond, J. A. Wilson, P. & DeVries, A. L. 1989 PNAS U.S.A. 86, 881–885).

Temperature fluctuations during transport and storage of frozen foods can result in numerous cycles of freeze-thaw. In a product like ice cream, this freeze-thaw causes an increase in ice crystal size and a subsequent degradation in texture and product quality (described as "icy", "grainy", or "loss of homogeneity"). This occurs at temperatures near the product's freezing point where an equilibrium between water in the solid and liquid phases occurs resulting in larger ice crystals growing at the expense of smaller ones. Ice cream manufacturers try to overcome this problem by storage and shipping product at very cold temperatures far below the product's melting point (−20° F.). However, once the product gets to the distributors, the stores, and to the customers' home frost-free freezer (0° F.), the manufacturer no longer has control of the product storage temperature and degradation of quality can occur rapidly.

Ice crystal growth is also a problem in many other frozen food products. For example, the cell structure in frozen baked breads and cakes is broken down and the product dehydrated by ice crystal growth (migration of the small homogeneous ice crystals to large heterogeneous ones) over time resulting in a degradation in texture. Ice crystals also destroy the viability of microbial organisms used in the preparation and processing of various foods. For example, in "live dough" bread and pizza products, the fermentative ability of yeast required to raise a previously frozen dough is reduced or destroyed because ice crystal growth rips apart the organisms' membranes, killing them. Also, live cultures of microorganisms (bacteria and yeast) used in the production of food products, such as yogurt, cheese, sausage, beer, wine, etc., must be continually propagated and maintained at high costs because freezing results in lost viability.

Ice crystals are also a problem in many non-food products. For example, in the biotechnology industry, microbial cell lines including bacteria, fungi, and animal cells (e.g., "monoclonal cell lines") are preserved by freezing, but by conventional methods, only a fraction of the cells survive. In the medical industry, a significant proportion of cells comprising the tissues of organs are destroyed by freezing, thus making frozen organs currently unsuitable for transplantation. In the paint industry, the freezing of latex paint results in the separation of pigments and binders from the solvent (water), destroying the homogeneity of the components, resulting in irreversible gelation. These are only a few of numerous examples of potential applications of antifreeze proteins.

Isolation and characterization of antifreeze proteins from different fish have established the existence of four distinct classes of antifreeze proteins, one class of antifreeze glycoproteins and three classes of antifreeze peptides. The antifreeze glycoproteins, (AFGPs) are naturally found in the Antarctic Nototheniid, *Dissostichis mawsoniarei*, and are glycotripeptide polymers of Alanine-Alanine-Threonine with a disaccharide linked to the Threonine residue. This series of eight glycopeptides range in size from 2,400 to 34,000 Da (DeVries, A. L. 1983. Annu. Rev. Physiol. 45, 245–260). The other three classes of antifreeze proteins (AFPs) consist only of amino acid chains, are rather diverse and include the alanine-rich AFPs, cysteine-rich AFPs and a third class that is neither rich in alanine nor cysteine (Hew, C. L. Scott, G. K. & Davies, P. L. in "Living in the Cold, Physiological and Biochemical Adaptation". eds Heller, H. D. et al. 117–123 Elsevier, New York, 1986; Hew et al. 1984, J. Chromatog. 296:213–219).

The cysteine-rich AFPs are naturally found in the sea raven and are 9,000 to 10,000 Da in size. The class of AFPs which is neither cysteine-rich nor alanine-rich is also the most diverse. The AFPs from the Antarctic and North Atlantic Zoarcids *Rhigophila dearborni*, *Macrozoarce americanus*, and *Austrolycicthys brachycephalus* are similar ranging from 61 to 64 nonrepeating residues, with 56% to 69% homology, and lacks both alpha and beta helical tertiary structure (Raymond, J. A. Wilson, P. & DeVries, A. L. 1989 PNAS U.S.A. 86, 881–885). In contrast, the AFP from the Cottid *Hemitripteris americanus* is 17,000 Da in size, has a non-repeating sequence without significant homology to the zoarcid sequences, and possesses both alpha and beta helical secondary structure (Ng, N. F. et al. 1986, J. Biol. Chem. 261, 15690–15695).

The alanine-rich AFPs are naturally found in the North Atlantic Cottid, *Myoxocephalus scorpius*, and the winter flounder *Pseudopleuronectus americanus*. This class of AFPs range in size from 2,900 to 10,000 Da depending on the method of measurement. These peptides have a common motif comprised of an 11 amino acid repeating sequence with high alanine content which is purported to contribute the antifreeze activity (Fourney et al. 1984, Can J. Zool. 62, 38–33). The winter flounder AFPs have been among the most thoroughly studied of the alanine-rich AFPs, and amino sequence analysis of the two most abundant AFPs, antifreeze protein component A and antifreeze component B (hereafter referred to as AFP A and AFP B), reveal that they each are comprised of 37 amino acids (containing three 11 amino acid repeats) resulting in a size of 3300 daltons.

The winter flounder, *Pseudopleuronectus americanus*, produces a class of at least seven closely related alanine-rich antifreeze proteins; however, two of the seven, AFP A and AFP B make up 55% and 35% of the total AFP mass, respectively Their amino acid sequences have been determined (Duman, J. G. and DeVries, A. L. 1976. Comp. Biochem. Physiol. 54B, 375–380; DeVries, A. L., and Lin, Y. 1977, Biochem. Biophys. Acta. 495, 388–392; and reviewed in Fourney et al. 1984, Can. J. Zool. 62, 28–33) and are taken from Pickett et al. (1984, Eur. J. Biochem. 143, 35–38). The amino acid sequence of AFP A is shown in SEQ ID NO:1. AFP B is identical to AFP A except that residue 18 is an Ala, not a Lys; residue 22 is a Lys, not a Glu; and residue 26 is an Asp, not an Ala.

The winter flounder AFP genes have been cloned and sequenced (Davies et al. 1982, PNAS U.S.A. 79, 335–339; Davies, P. L. et al. 1984, J. Biol. Chem. 259, 92419247 ; Pickett et al. 1984, Eur. J. Biochem. 143, 35–38; Scott, G. K., Hew, C. L., and Davies, P. L., 1985, PNAS U.S.A. 82, 2613–2617; Fourney et al. 1984, Can. J. Zool. 62, 28–33). From the DNA sequence information, it was deduced that the AFP gene has an intervening sequence which is removed during DNA maturation and that AFP is synthesized as an 82 amino acid preproprotein. A typical winter flounder AFP gene DNA sequence encoding AFP A is taken from Scott et al. 1988 (J. Mol. Evol. 27, 29–35) and reported at SEQ ID No:2 and at FIGS. 5a–5d

The promoter (TATAAAA), transcription start site (+1, A), translation termination codon (TAA), and polyadenylation signal (GAATAAA) are underlined in FIG. 5a–5d. The intervening sequence is written in lower case letters, and the predicted sequence for the gene product is shown above the DNA sequence. The predicted 82 amino acid preproprotein sequence encoded by this gene is identical to antifreeze protein A preprotein isolated from winter flounder (Davies et al. 1982, PNAS U.S.A. 79, 335–339).

The genome arrangement of the winter flounder AFP genes have been studied in detail and are found to make up a multigene family of AFP genes, each comprising about 1000 base pairs of DNA tandemly linked and clustered in the genome (Davies et al. 1984, J. Biol. Chem. 259, 9241–9247; Scott et al. 1985, PNAS U.S.A. 82, 2613–2617; Scott et al. 1988, J. Mol. Evol. 27, 29–35). Studies in winter flounder (Hew et al. 1978, Biochem. Biophys. Res. Commun. 85,421–427; Pickett, et al. 1983, Biochem. Biophys. Acta 739, 97–104) revealed that an 82-residue preproprotein is synthesized in the liver where it is processed to a 59 residue proprotein which in turn is secreted into the serum. In the serum the 59-residue proprotein is matured to the most abundant species, a 37-residue AFP (i.e., AFP A and B). Fractionation of fish serum using Sephadex G75 chromatography followed by Reversed Phase-HPLC however, resolves seven active AFPs, AFP A and B along with five other less abundant species (Fourney et al. 1983, Can. J. Zool. 62, 28–33). One of the other five active AFPs is a 36-residue version of AFP A lacking the C-terminal (37th amino acid) Arginine residue (Pickett et al. 1984, Eur. J. Biochem. 143, 35–38; Fourney et al. 1984, Can. J. Zool. 62, 28–33;).

One method to determine if a molecule has antifreeze protein activity is to measure the thermal hysteresis of a solution in which AFP has been added (Fourney et al. 1983, Can. J. Zool. 62, 28–33). Thermal hysteresis is defined as the difference between the freezing and melting temperatures of a solution. As stated previously, AFP lowers the freezing point of a solution in a non-colligative manner resulting in little or no effect on the melting point. Hence, an AFP solution may have a freezing point of -2° C., but a melting point of -1° C. In contrast, salts typically depress the freezing point and melting point equally. Another method for assessing AFP efficacy is to monitor the rate of ice crystal growth and morphology microscopically (Raymond et al. 1989, PNAS U.S.A. 86, 881–885). Ice crystals formed in aqueous solutions grow rapidly, particularly near the melting point; the addition of low levels of AFP drastically reduces the growth rate resulting in smaller ice crystals. However, the art lacks an efficient way to assay for the presence of AFP.

Due to the novel properties that AFP imparts to solutions and particularly its ability to reduce the rate of ice crystal growth, it may have many applications in food, beverage, and non-food products. As a first step, a plentiful supply of antifreeze protein is required to utilize it as a research tool to investigate its applicability as a product ingredient. Although AFP makes up as much as 1% of the winter flounder serum protein in the mid-winter months, the level drop by 100 fold the rest of the year and it is not possible nor commercially feasible to obtain the large quantities which would be required for a single commercial application, such as the frozen food industry. In fact, AFP has not been commercially tested previously because it has not been practical to obtain large enough quantities from fish. Recombinant DNA technology provides a viable alternative Recently, Peters et al. (1988, Advances in Gene Technology: Protein Engineering and Production, Proceedings of the 1988 Miami Bio/Technology Winter Symposium, ICSU Short Reports Volume 8) reported the cloning and expression of a winter flounder antifreeze proprotein in *E. coli*, as a Lac Z-proAFP hybrid peptide. After purification of the hybrid Lac Z-proAFP, the Lac Z portion is removed by digestion with a protease (coagulation factor Xa; Nagai, K. & Thogerson, H. C. 1984, Nature 309, 810–812). In this case, the goal of Peters and coworkers was to obtain experimental quantities of the proAFP sufficient to study the winter flounder AFP processing system.

Yeast is considered to be a better host organism for the production of food ingredients because it is a GRAS (generally regarded as safe) organism and it can be made to express, properly process and secrete some heterologous proteins. The problem is that some proteins cannot be produced in yeast (e.g., some are toxic), and others cannot be properly processed and/or secreted. Each protein must be handled on a case by case basis with the probability of success impossible to predict a priori. Another problem is that yeast and winter flounder have different codon preferences and hence obtaining efficient translation of the natural winter flounder gene in yeast is unlikely. This problem can be overcome by direct chemical synthesis of the AFP gene using codons preferred by yeast. Another problem is that the natural winter flounder genes have intervening sequences and the RNA's they encode are unlikely to be properly processed by yeast; and hence obtaining a mature antifreeze protein via expression of a natural winter flounder gene in yeast is unlikely. Again, chemical gene synthesis can overcome this problem by eliminating the intervening sequence from the yeast AFP gene version. Also, the natural winter flounder gene encodes an 82 amino acid preproprotein which in the flounder undergoes a series of proteolytic processing steps to arrive at the mature 37 amino acid active peptide; if produced intracellularly in yeast, it is unlikely that the preproprotein would be processed properly. One approach is the chemical synthesis of a gene lacking the 45 amino acid prepro region, however this would require a Met-residue at the N-terminus. Alternatively, a hybrid gene could be constructed to encode a hybrid protein which can be produced with a convenient proteolytic cleavage site between the leader protein and the N-terminal Asp-residue. Once isolated, the hybrid protein can be processed in vitro.

Another approach is to direct yeast to secrete AFP. One problem is that the natural 45 amino acid winter flounder leader sequence may not function as a secretion and processing signal in yeast since it does not contain the proper processing signal amino acids (e.g., LysArg, ArgArg, or LysLys) between amino acids 45 and 46 to signal the processing necessary to give the desired maturation product. In addition, yeast have no natural processing enzyme to remove the C-terminal Gly, residue 82, of the nascent peptide. Another approach is to chemically synthesize the AFP gene and combine it with a natural yeast expression, processing and secretion system such as the *Saccharomyces cerevisiae* mating factor alpha one system, resulting in a hybrid gene which encodes a hybrid protein with the proper yeast processing and secretion signals. This requires that the DNA region encoding the mature protein (e.g., alpha factor) be removed and replaced with DNA encoding the mature AFP. The problem is that simple replacement with a heterologous gene may not result in secretion and/or proper processing.

SUMMARY OF THE INVENTION

A plentiful supply of antifreeze protein is required to utilize it as a research tool and possible product ingredient This invention is based on the discovery that yeast can be made by recombinant DNA technology by those skilled in the art to express, properly process, and secrete anti-freeze proteins, that are heterologous to yeast, in a discrete form without unwanted polypeptide presequence or other artifacts of expression. By the term "heterologous" as used herein is meant that the protein is not normally produced by or required for viability by yeast.

In the method of the present invention, viable yeast cells are transformed with expression vectors containing a yeast secretion signal sequence combined appropriately with a chemically synthesized gene encoding an antifreeze protein. The yeast cells are cultured under conditions suitable for expression of the antifreeze protein and the antifreeze protein is secreted by the yeast into the medium. The antifreeze protein is recovered from the medium in the native form without the need to remove unwanted presequence or other artifacts of expression (e.g., the methionine attached to the otherwise first N-terminal amino acid which is an expressional consequence of the AUG translational start signal codon). The antifreeze protein, after purification, is fit for use as intended.

The present invention is also three DNA sequences that when transferred to yeast via an appropriate expression vector are capable of directing the synthesis, processing and secretion of antifreeze proteins. The present invention teaches how to produce antifreeze proteins with amino acid sequences which are not identical to that of the winter flounder antifreeze protein, AFP A. More specifically, the present invention describes DNA sequences and methods for combining them to manufacture hybrid antifreeze protein genes which are expressed, properly processed and secreted as a 37 amino acid antifreeze protein by yeast. Antifreeze proteins capable of producing larger (>37 amino acids) or smaller (<37 amino acids) AFP's are easily conceived.

The present invention also provides methods to recover significant quantities of the recombinant antifreeze proteins produced by yeast from fermentation broth. The present invention is also a method for assaying for the presence of AFP.

Antifreeze proteins produced by this invention are identical to the matured 37 amino acid winter flounder AFP A in 36 of the 37 amino acids, due to the discovery that the *E. coli* recombination system, which is used during one of the steps in molecular cloning, randomly mutates the AFP DNA sequence at a high frequency resulting in a family of antifreeze protein genes. Active antifreeze proteins smaller than 37 amino acids with one or more of the biochemical and physiochemical properties of AFP A are also produced and can be recovered by this invention. For example, antifreeze proteins with as few as 17 amino acids and having the sequence of the first 17 of the 37 amino acids shown in SEQ ID NO:1 were isolated and found to be highly active. The antifreeze proteins produced and purified as described by the present invention are extremely efficacious in controlling ice crystal size and migration (larger crystals growing at the expense of smaller ones) in frozen novelty desserts.

Other aspects and advantages of the present invention will be apparent upon consideration of the following detailed description thereof.

BRIEF DESCRIPTION OF THE DRAWINGS

In the drawings:

FIG. 1 shows the sequence of the hypothetical hybrid gene responsible for expression of a hybrid protein which is properly processed and secreted as a fully mature and functional AFP.

FIG. 3 shows the DNA sequence (and the amino acid sequence it encodes) of a synthetic AFP gene used in the construction of a hybrid AFP gene which can be expressed in yeast.

FIG. 4 shows oligonucleotides SEQ ID NO: 3,6, and 7 used for the assembly of an AFP gene.

FIG. 5 show the gene sequence of the winter flounder AFP A gene.

DETAILED DESCRIPTION

Figure 2:
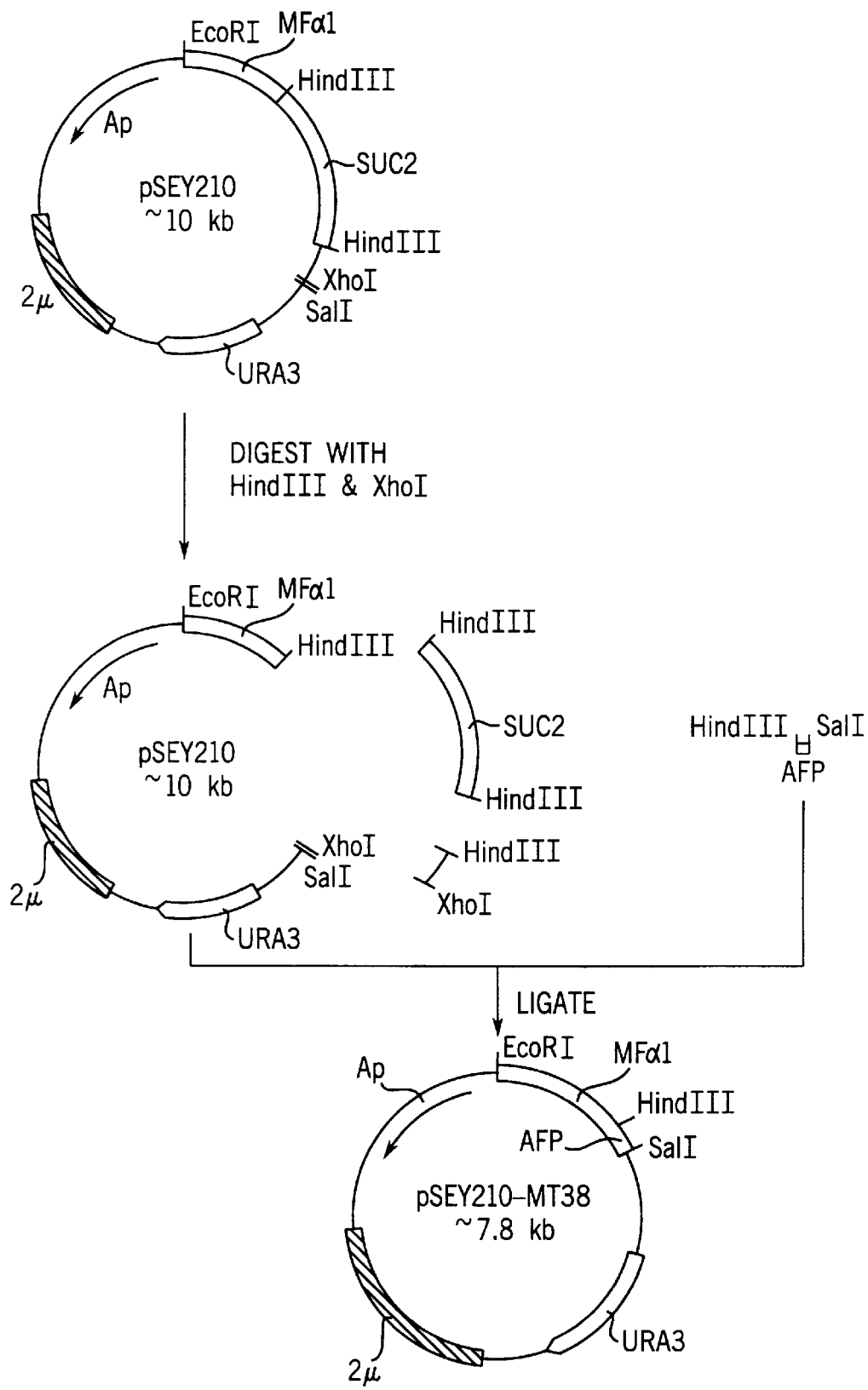
FIG. 2 illustrates an example of an operational sequence of steps—starting with one (pSEY210) of many possible expression/secretion vectors—which can be used to construct a hybrid AFP gene. By this example, the resident SUC2 is excised using HindIII and XhoI restriction endonucleases and replaced with an appropriately designed synthetic AFP gene with compatible ends. The resulting plasmid (by this example, pSEY210-MT38) when introduced into an appropriate yeast is capable of directing the expression, processing and secretion of AFP A.

The following example illustrates a preferred general procedure for design, preparation and assembly of deoxyoligonucleotides for use in the manufacture of antifreeze protein DNA sequences of the invention.

Herein, the term "manufactured" as applied to a DNA sequence or gene shall designate a product either totally chemically and enzymatically synthesized by assembly of nucleotide bases or derived from the biological replication of a product thus synthesized. As such, the term is exclusive of products "synthesized" by cDNA methods or genomic cloning methodologies which involve starting materials which are initially of biological origin.

The following abbreviations shall be employed herein to designate amino acids: Alanine, Ala; Arginine, Arg; Asparagine, Agn; Aspartic acid, Asp; Glutamic acid, Glu; Glycine, Gly; Leucine, Leu; Lysine, Lys; Methionine, Met; Serine, Ser; Threonine, Thr and Valine, Val.

EXAMPLE 1
Design, Synthesis, and Assembly of an AFP Gene

It was the general strategy to manufacture a hybrid AFP gene comprised of DNA encoding a protein with three major feature segments—a secretion leader to direct proper translocation to the membrane and direct secretion; the mature 37 amino acid form of an AFP A-like antifreeze protein; and a junction/processing peptide between the secretion leader and the antifreeze protein to direct cleavage of the hybrid protein resulting in an AFP A-like protein. (By AFP A-like protein, we mean a protein identical to AFP A except for one amino acid residue.) These three features are explained in more detail as follows:

(i) For the secretion leader portion of the hybrid protein gene, DNA encoding the yeast prepro region of the mating factor alpha one protein was used because this prepro portion targets hybrid proteins for secretion (for a detailed specific example see Brake et al., 1984, PNAS U.S.A. 81, 4642–4646; for a review see Das, R. C. and Sheltz, J. L. 1987, Biotech. Prog. 3, No.1, 43–48). It is conceived that other secretion leader sequences may also function in this regard.

(ii) For the "secretion product" portion of the hybrid protein gene, DNA was used which encodes a protein that is identical to the natural AFP A protein in 36 out of the 37 residues of AFP A, the DNA sequence of which was inferred from the amino acid sequence which has been reported by Pickett et al. (1984, Eur. J. Biochem. 143, 35–38).

(iii) In order to obtain proper processing of the hybrid protein (removal of the prepro secretion leader prior to secretion), DNA encoding a protease recognition sequence was used at the junction between the prepro segment and the AFP A segment comprising a natural yeast protease cleavage site (e.g., in this case, the yeast KEX2 protease cleaves at the C-terminus of the second basic residue of LysArg-COOH; amino acids −2 and −1 in FIG. 3; this approach has been shown to work for other proteins, see Brake et al., 1984, PNAS U.S.A. 81, 4642–4646), with the N-terminus or number 1 amino acid of AFP A-like protein exactly adjacent the C-terminus of a yeast protease cleavage site (e.g., LysArg-COOH; FIG. 3). Hybrid antifreeze protein genes using other secretion leader sequences employing other protease recognition sites also may be used.

Specifically designed was a synthetic gene encoding a DNA sequence containing *Saccharomyces cerevisiae* codon preferences according to Bennetzen et al. (1982, J. Biol. Chem. 257, 3026–3031) for the mature form of the natural antifreeze protein A (AFP A) amino acid sequence as reported by Pickett et al. (supra). In certain cases, codons were employed to introduce unique restriction sites to facilitate assembly of the oligonucleotides (e.g., DdeI site between the two halves of the gene) and molecular cloning of the assembled AFP A gene into a yeast expression vector. For example, an AFP A gene was designed to have a unique HindIII site at the 5' end and unique BamHI, EcoRI, and SalI sites at the 3'end of the gene to facilitate molecular cloning (e.g., SEQ ID NO:3).

SEQ ID NO:3 and FIG. 3 show the assembled oligonucleotides encoding an AFP A-like DNA with unique restriction sites and encoding an N-terminal yeast protease processing recognition site. (SEQ ID NO: 3 and FIG. 3 correspond to AFP A(38) and show a one base change from the oligonucletide-encoded sequence. This origin of this change is discussed above.)

Synthesis of DNA encoding an AFP A gene was carried out. Important features to note include: (i) addition to the N-terminus of the AFP A sequence is AlaSerLeuAspLysArg which results in a HindIII compatible site (AGCT) at the 5' end of the gene to facilitate molecular cloning and to create a KEX2 protease cleavage site which eliminates N-terminal heterogeneity (i.e., so inefficient processing of the GluAla-GluAla alpha factor leader is not a problem); (ii) EcoRI and BamHI sites at the end of the AFP A gene to facilitate subcloning into other vectors and to act diagnostically in restriction mapping; and (iii) a SalI 5' single stranded termini at the end of the AFP A gene which is compatible with, and clonable into the XhoI site of pSEY210.

The oligonucleotides were chemically synthesized per our design and specifications under contract with Cornell University by standard methods and purified by Reversed Phase High Performance Liquid Chromatography (RP-HPLC). The AFP A gene was synthesized in four single stranded fragments designated fragments 1, 2, 3, and 4 and shown in FIG. 4 and SEQ ID NOs:4, 5, 6, and 7.

Cloning strategy

The following general cloning strategy can be used. In general, the AFP A synthetic DNA fragment with the HindIII and the SalI ends can be cloned into plasmid pSEY210 at the HindIII/XhoI sites (Emr et al., supra) as diagrammed in FIG. 2. In general, the following steps can be employed. In step 1, pSEY210 (the pertinent restriction sites are shown in FIG. 2) can be co-digested with HindIII and XhoI restriction endonucleases (using the same buffer), excising the resident DNA encoding a portion of the SUC2 gene, and leaving the vector with HindIII/XhoI "sticky ends" to clone into. In step 2, the digestion mixture can be phenol extracted and a sample run on an agarose gel to verify that digestion occurred. In step 3, the AFP A HindIII/SalI DNA can now be ligated to the HindIII/XhoI digested vector pSEY210. The HindIII "sticky ends"of the AFP A gene and pSEY210 anneal and ligate as do the SalI and XhoI overhangs (SalI and XhoI sites are compatible, however upon ligation, both sites are lost). In step 4, the ligated DNA can be digested with XhoI (the desired AFP A plasmid construct will no longer have an XhoI site and hence be unaffected). This step eliminates the possibility of the previously excised DNA fragment from the parent plasmid pSEY210 (which contains an XhoI site) from re-cloning (linears will not transform *E. coli* efficiently and therefore will be a rare and usually undetectable class of transformant). Hence, this step accomplishes two goals: (i) eliminates vector:vector cloning; and (ii) eliminates the possibility of re-cloning the previously excised fragment which contains an XhoI site. In step 5, the XhoI treated DNA can now be used to transform *E. coli*. In step 6, in theory, most of the transformants should carry the desired AFP A plasmid synthetic DNA insert as shown in FIG. 3 and thereby resulting in the construction of a hybrid gene as shown in FIG. 1. This is generally confirmed by screening and subsequent restriction mapping analysis (e.g., the desired plasmid construct should have a unique BamHI site, FIG. 2) of the plasmids carried by the E. coli transformants Finally in step 7, plasmid DNA can be made and used to transform appropriate yeast.

Before the AFP A gene can be molecularly cloned as described immediately above, the synthetic DNA fragments (SEQ ID NOS: 4, 5, 6, 7) can be preassembled by standard annealing and ligation methodology used by those skilled in the art and essentially as described in Maniatis et al., (1982, Molecular Cloning: A Laboratory Manual, Cold Spring Harbor Laboratory, N.Y.). Examples of two strategies which can be used to assemble the fragments encoding the AFP A gene are described below. Of course, if one wished to reproduce the mutations found in our three AFPs, AFP A(10), AFP A(38), and AFP A(42), one would substitute an oligo with the desired mutation for those described in FIG. 4.

In the first approach, the complementary single stranded fragments (FIG. 4; fragment 1 is complementary to fragment 3; fragment 2 is complementary to fragment 4) of each half of the AFP A gene (HindIII to DdeI and DdeI to SalI); can be annealed by mixing the complementary fragments in an equimolar ratio and then heating to 100° C. for 5 minutes, and allowing them to cool slowly to room temperature. That the fragments indeed annealed can be confirmed by examining their mobility by agarose gel electrophoresis using a 3% agarose gel and appropriate size standards. After the annealing reaction, the double stranded fragments will run at a higher mobility than the non-annealed single stranded fragments. The annealed but non-phosphorylated fragments can be mixed at various molar ratios with the vector pSEY210 (FIG. 2) which has been previously digested with HindIII and XhoI. T4 DNA ligase is then added and the reaction allowed to proceed for 16 hours. Since only the vector 5' HindIII and XhoI sites are phosphorylated, ligation can only occur between the synthetic AFP A gene HindIII and SalI fragments and the vector; the termini within the AFP A fragment cannot ligate. This eliminates tail to tail (e.g., HindIII—DdeI-DdeI—HindIII or SalI—DdeI-DdeI—SalI) ligation of the same fragment from occurring. The ligation mix is then diluted 10 fold with ligation buffer to reduce the concentration of vector and insert. T4 polynucleotide kinase is then added to phosphorylate the DdeI termini; the reaction is carried out at 37° C. for 1 hour. Additional T4 DNA ligase is then added and the reaction carried out for 16 hours. Because of the dilution step, the intramolecular ligation event (vector with itself containing the HindIII—DdeI fragment ligated to the vector HindIII site and the DdeI—SalI fragment ligated to the XhoI site) is favored. This ligation mix is then used to transform E. coli HB101 (Bolivar et al., 1977, Gene 2, 95–113) as described in Maniatis et al., (1982, Molecular Cloning: A Laboratory Manual, Cold Spring Harbor Laboratory, N.Y.). In one such experiment, thirty-three single isolate transformants were obtained by practicing this first approach.

The second approach involved first phosphorylating the 5' end of the DdeI single stranded fragments (fragments 2 and 4; FIG. 4), then annealing the complementary strands (fragments 1 and 3; fragments 2 and 4; FIG. 4) and ligating the two synthetic AFP A gene halves together. The ligated fragments (comprising the assembled synthetic AFP A gene) can then be mixed with vector pSEY210 pre-digested with HindIII and XhoI as described above, T4 DNA ligase added and the mix incubated overnight. The ligation mix is then heated to 100° C. for 5 minutes to melt off the unligated strands and rapidly cooled by dilution with 0.5 ml of Tris EDTA buffer. This mix can be used to transform E. coli HB101. In one such experiment, fifteen single isolate transformants were obtained by practicing this second approach.

Putative AFP A transformants can be screened as follows. Plasmid DNA mini-preparations can be made by standard methods as described in Maniatis et al., (1982, Molecular Cloning: A Laboratory Manual, Cold Spring Harbor Laboratory, N.Y.) from the transformants obtained from the approaches described above. The plasmids are screened for those containing the AFP A DNA insert by digestion with EcoRI; pSEY210 contains a single EcoRI site while the desired AFP A DNA replacement (which also contains an EcoRI site) will contain two EcoRI sites. Hence, plasmids containing the synthetic AFP A DNA insert will show two fragments by agarose gel electrophoresis while those without the AFP A DNA insert, only one. The majority of the plasmids are expected to show an AFP A DNA insert by this criteria. These plasmids can then be further characterized by restriction analysis. Each plasmid is digested with various restriction endonucleases and the fragments analyzed by agarose gel electrophoresis. By the restriction mapping criteria, the plasmids of interest and the vast majority obtained by these approaches are identical to pSEY210 except in the region of the gene replacement.

Next, the region within the AFP A DNA insert should be restriction mapped to determine if the AFP A DNA fragment is intact. For example, it is important to determine if the DdeI site in the middle portion of the AFP A DNA insert exists, and to determine the size of the fragments HindIII to DdeI and DdeI to BamHI (FIG. 3) to confirm that no major recombinational events (e.g., deletions, insertions, rearrangements) have occurred.

Surprisingly, while first practicing this invention, this latter step—restriction and size analysis of the HindIII/EcoRI fragment originally containing the entire synthetic AFP A DNA—led to an important discovery. In practice, an unexpectedly and amazingly wide variety of AFP A DNA insert sizes are found among the recombinant plasmids, ranging in size from about 20% that are much smaller than expected, about 45% that are slightly smaller than expected, to about 35% that are of the expected size. These results show that the synthetic AFP A (FIG. 3) molecularly cloned by the approaches described above is extremely recombinogenic in E. coli HB101. When these same covalently closed, supercoiled plasmids are used to retransform E. coli HB101, and plasmid DNA is reisolated, no change in the originally isolated plasmid AFP A DNA is normally detected by restriction analysis (e.g., plasmids originally with large inserts still have the same large inserts). This result indicates that the extraordinary level of recombination occurs as a result of the nature of the state of the chemically synthesized AFP A DNA present in the ligation and transformation mix, since this does not occur at high frequency when the same plasmid DNA, but covalently closed and supercoiled (as isolated from the original transformant) is used to retransform E. coli HB101. This discovery first led to the idea that this methodology may be useful for generating families of genes with varying degrees of deletion mutations, starting from a parent DNA. Based on restriction analysis, it is not possible at this point (unless a point mutation occurs at a restriction site) to determine if point mutations are also occurring at high frequency; however, this is consistent with the discovery.

To determine if the recombinant plasmid candidates (as determined by restriction mapping and size analysis) carrying the synthetic AFP A DNA inserts are capable of directing the expression, processing and secretion of AFP A in yeast, the recombinant plasmids can be transferred to *Saccharomyces cerevisia* yeast (2102) via transformation as described by Hinnen et al. (1978, PNAS U.S.A., 75, 1929–1933) which is incorporated by reference herein. Several different plasmid candidates should be evaluated in yeast. This can be done by culturing a given yeast transformant (containing a given plasmid candidate) in 200 ml of MIN+CAA (0.67% yeast nitrogen base without amino acids, 2% dextrose, and 1% casamino acids) in 1 liter baffled flasks at 30° C. with rapid shaking for 48 hours. The yeast cells can be removed from the fermentation broths by filtration using a 0.45 $\mu$m nitrocellulose membrane, and the peptides in the clarified broths can be concentrated by adsorption to C18 (Octadecyl C18 disposable extraction columns, J. T. Baker Inc.). The peptides can be eluted from the C18 with 3×1 ml 20% water/80% acetonitrile, 0.1% trifluroroacetic acid (TFA). The volume of the eluant can be reduced to about 0.5 ml using a stream of nitrogen, and the concentrate subjected to dialysis (1000 MW cut off) overnight.

The dialysates can be analyzed by three methods.

(i) Reversed Phase High Performance Liquid Chromatography (RPHPLC) can be employed to determine if the dialysates contain peptides with retention times similar to a chemically synthesized AFP A standard.

(ii) The dialysates can be tested for functionality by examining their effect on ice crystal morphology; when water containing concentrations of the chemically synthesized AFP A standard above 1 $\mu$g/ml is frozen, the ice crystals which form have characteristically distinguishing sharp facets. We have found this test difficult to analyze.

(iii) The dialysates can also be analyzed for functionality by examining their effect on ice crystal size and growth rate in a sucrose solution. A given dialysate may be further analyzed by serially diluting (1:2) it with a sucrose stock solution (final concentration of sucrose maintained at 20%) containing 2 $\mu$m glass beads. A drop of the test solution (containing glass beads as spacers) is spotted on a 15 mm round glass cover slip and a second cover slip is placed on top of the solution, sandwiching it between the two cover slips. Any excess solution is removed by blotting the cover slips between two filter papers. The cover slips containing the test solution are then placed on a cold stage which is enclosed in a mini-environmental chamber constantly purged with nitrogen gas to remove moisture and reduce condensation. The cold stage mini-environmental chamber can be mounted on a microscope with a 40× long working distance objective. The cover slip containing the test solution is placed on the cold stage and supercooled to −25° C. which results in freezing of the sample. The temperature of the frozen test solution is then rapidly increased to −5° C. and the size of the growing ice crystals is monitored microscopically and recorded by Polaroid photography (400×) over a period of routinely 30 minutes and occasionally up to 3 hours. Photographs showing the size of the ice crystals formed after a given period of time by the (i) 20% sucrose control, (ii) synthetic AFP A standards in 20% sucrose (ranging from 1 $\mu$g/ml to 100 $\mu$g/ml), and (iii) the test solutions can be compared and the functional AFP A concentration of the experimental test solutions estimated. For example, if the ice crystal size of a test solution is similar to that of a standard synthetic AFP A solution at 20 $\mu$g/ml, then the functional AFP concentration of that test solution is estimated at 20 $\mu$g/ml.

Another test can also be utilized, termed the "Cronan Thaw/Freeze Test." This test is based on the observation that AFPs at concentrations down to 1 to 2 $\mu$g/ml reproducibly and characteristically effect the morphology of the ice crystals in sucrose solutions, making the ice crystals form distinctive hexagonal crystals. This test is performed by freezing the test solution as described above, allowing the ice crystals to grow at a temperature 1 to 2 degrees below the melting point (routinely −5° C.) for a few minutes, raising the temperature to the melting point for 15 to 20 seconds to partially melt existing ice crystals, and then lowering the temperature back 1 to 2 degrees below the melting point; just as refreezing occurs, the distinctive hexagonal shape is easily seen at AFP concentrations at or above 1 to 2 $\mu$g/ml.

Figure 6A:
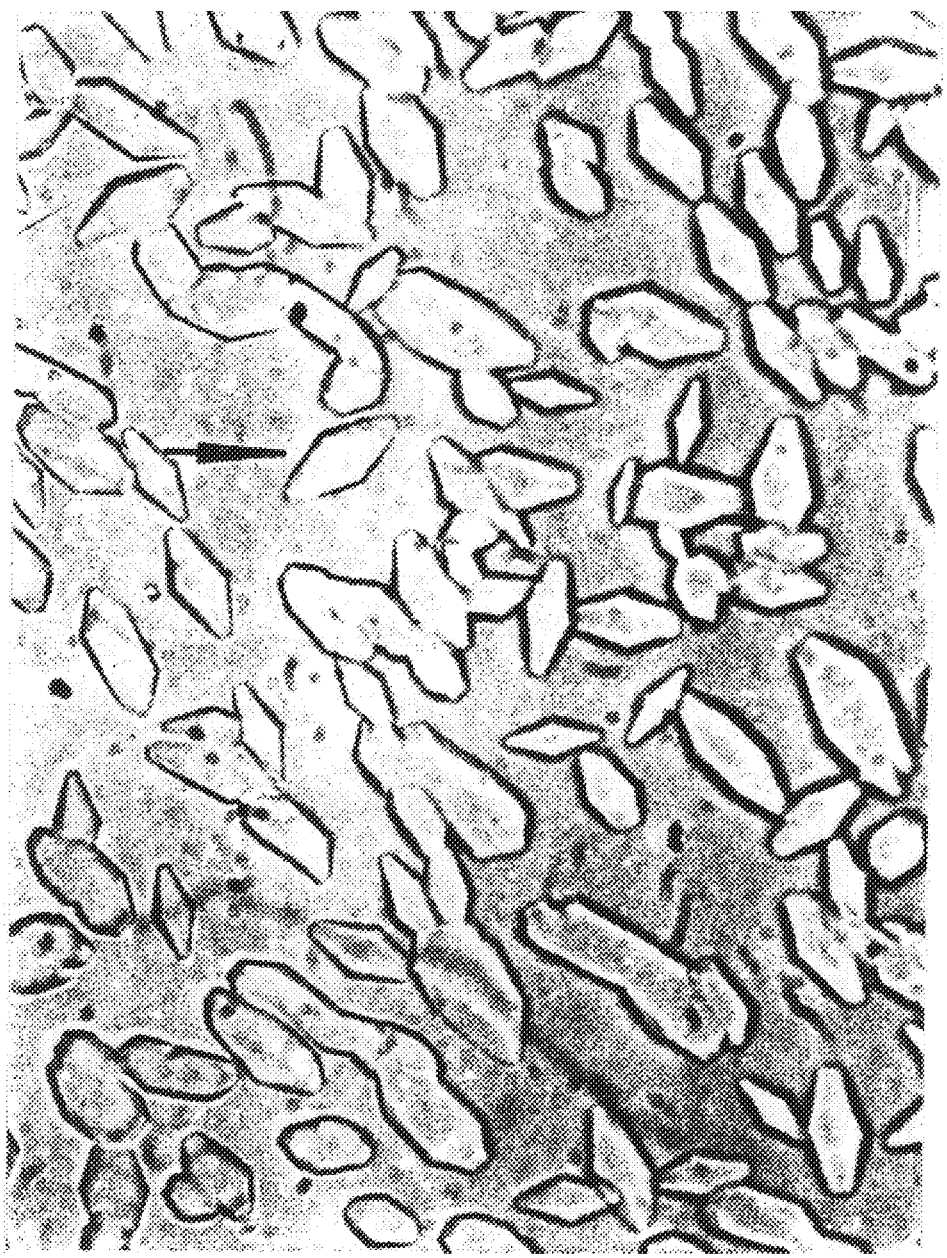
FIG. 6 parts A–C is a set of photographs showing the results of a "Cronan Thaw/Freeze" AFP assay.
Figure 6B:
Figure 6C:
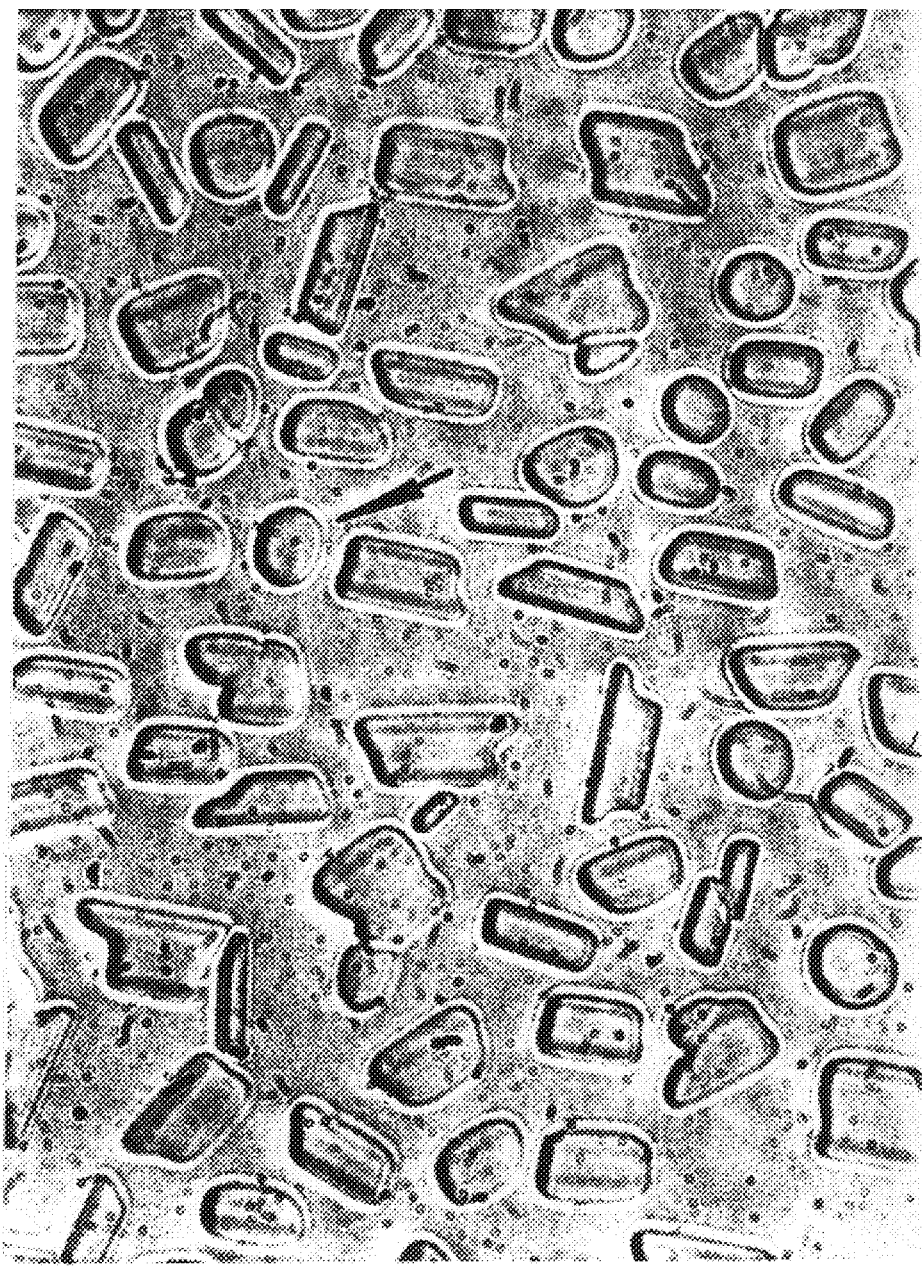

FIG. 6 is a photograph (400×) of representative hexagonal crystals. FIG. 6A represents a concentration of AFP at approximately 10–20 ppm, and FIG. 6B represents a concentration of AFP at approximately 5 ppm. FIG. 6C is a blank control. At low concentrations, the hexagons disappear after about a minute, however at high AFP concentrations (above 10 $\mu$g/ml) they remain for several minutes. Preferably, the sucrose-containing solution is 5%–40% sucrose. Most preferably, the solution is 20% sucrose.

The Cronan Thaw/Freeze test provides a functional assay that would be expecially useful if AFP concentrations were to be determined in a situation, such as organ preservation, where the integrity of an AFP-containing solution is vital. We envision that the Cronan Thaw/Freeze assay is suitable for all AFPs, not just the AFPs we have examined.

Serially diluting a given test sample until the "Cronan Thaw/Freeze Test" is negative can also be used to estimate AFP concentration. One dilution above a negative result is interpreted as equivalent to 1 to 2 $\mu$g/ml and the resultant concentration can be calculated accordingly. By comparing the AFP concentration obtained by the RP-HPLC method with the amount determined by the functionality test, the efficacy of a given AFP can be determined.

Yeast transformants carrying plasmids with the synthetic AFP A DNA insert of the correct size (based on restriction analysis) can be evaluated for their ability to produce and secrete functional antifreeze protein (based on RP-HPLC retention time and functionality) by the criteria as described above. In practice, half of the yeast transformants carrying plasmids of the correct size are found to produce functional AFP and fall into groups, with a given group producing a functional AFP with a characteristic RP-HPLC profile (based on RP-HPLC profiles).

The different groups of functional AFPs (based on RP-HPLC profiles) produced by these transformants were found to result from a single amino acid change in the protein sequence as a result of a point mutation which occurred within the AFP gene during the course of molecular cloning. Hence, in order to find the transformant which produces the desired AFP sequence, it is necessary to evaluate a representative number of yeast transformants and sequence the AFPs that they produce. At this stage, one has transformants carrying recombinant plasmids representing a family of AFP genes and which direct the expression and secretion of a family of AFPs.

Functional antifreeze protein produced by yeast transformants in each representative group (based on RP-HPLC profile) should be isolated, purified and sequenced. The following method can be employed.

Two thousand ml of broth fermented by each yeast transformant as described previously is clarified by filtration through a 0.45 $\mu$M nitrocellulose membrane and the AFP concentrated by C18 mini-column chromatography (high capacity Octadecyl C18 disposable columns, J. T. Baker), 250 ml/column. The adsorbing fraction is eluted with 3×1 ml 20% water/80% acetonitrile, 0.1% TFA as described previously The volume of the eluant is reduced to about 0.5 ml under a nitrogen stream. The concentrates are then separated on a 1.5×26 cm Biogel P2 size-exclusion chromatography column using water as an eluant and fractions collected. Fractions are assayed and those containing functional material are applied to a Pharmacia HR 10/10 column packed with DEAE-Fractogel. The adsorbing fractions are eluted with a linear gradient consisting of 0.001M Tris and to 0.001M Tris, 0.1M NaCl. Fractions are collected, and aliquots of each fraction are analyzed by RP-HPLC. The fractions containing peptides with the appropriate retention time are re-concentrated by C18 column chromatography as described above, the adsorbing material is eluted and the volume reduced with nitrogen as before. The peptides in the concentrated eluant are separated by RP-HPLC and fractions are collected and re-analyzed by RP-HPLC. Fractions containing material of a single RP-HPLC peak are re-tested to confirm functionality, as described previously. The aqueous AFP samples can be maintained frozen at this stage without loss of activity. The functional, purified AFP is then subjected to quantitative amino acid analysis and amino acid sequence analysis.

The following is an example of a family of antifreeze proteins that can be generated as a result of practicing this invention. The antifreeze proteins produced by three different yeast transformants 2102-pSEY210-MT10-8, 2102-pSEY210-MT38-3, and 2102-pSEY210-MT42-1 (generated by transforming yeast with three different plasmid candidates) were studied in detail. These transformants are representatives of three different groups of transformants producing AFPs which possess functional antifreeze protein activity but have different RP-HPLC profiles. Each AFP species was isolated from a fermentation broth fermented by one of the three transformants, purified (as described above), and the purified AFPs subjected to total amino acid analysis and amino acid sequence analysis.

From these analyses, the following conclusions can be drawn: yeast transformant 2102-pSEY210-MT10-8 produces a functional antifreeze protein identical to winter flounder AFP A (SEQ ID NO:1) except asparagine replaces leucine at residue 23. Yeast transformant 2102-pSEY210-MT38-3 produces a functional antifreeze protein identical to winter flounder AFP A except that valine replaces alanine at residue 36. Yeast transformant 2102-pSEY210-MT42-1 produces a functional antifreeze protein with an identical sequence to winter flounder AFP A except threonine replaces alanine at residue 11. Table 1 and SEQ ID NOs:8, 9 AND 10 describe these sequences.

These purified antifreeze proteins from 2102-pSEY210-MT10-8, 2102-pSEY2IO-MT38-3, and 2102-pSEY210-MT42-1, when evaluated for functionality are similarly efficacious in controlling ice crystal growth by the sucrose ice crystal control test. That is, at an equal AFP concentration as determined by total amino acid analysis and RPHPLC, the average size of the ice crystals in a 20% sucrose solution after 30 minutes at −5° C. is the same, and many times smaller than the sucrose control.

For clarity, we refer to the protein isolated from 2102-pSEY210-MT10-8 as AFP A(10). The similar nomenclature of the other AFP proteins is described in Table 1.

TABLE 1

AMINO ACID SEQUENCE ANALYSIS OF EXPERIMENTAL PEPTIDES MADE BY AFP YEAST.

| YEAST TRANSFORMANT | SEQUENCE OF SECRETED AFP RECOVERED |
|---|---|
| | 1         10         20         30         37 |
| 2102-pSEY210-MT10-8 (SEQ ID NO:8, AFP A(10)) | DTASDAAAAA ALTAANAKAA AENTAANAAA AAAATAR |
| 2102-pSEY210-MT38-3 (SEQ ID NO:9, AFP A(38)) | DTASDAAAAA ALTAANAKAA AELTAANAAA AAAATVR |
| 2102-pSEY210-MT42-1 (SEQ ID NO:10, AFP A(42)) | DTASDAAAAA TLTAANAKAA AELTAANAAA AAAATAR |

The following example illustrates preferred methods for pilot scale production of AFP.

EXAMPLE 2

Pilot scale production and recovery of yeast AFP

Yeast Inoculum for Large Scale AFP Fermentations. To reduce the possibility of variability due to the inoculum for large scale fermentations, multiple 10 ml glycerol stocks can be made and stored at −70° C. The stocks can be produced as follows. A single colony of the desired AFP yeast transformant (e.g., 2102-pSEY210-MT-38-3, AFP A(38)), is streaked on SCM-bases agar, incubated for 48 hours at 30° C. and several individual colonies are picked and grown up in fermentation broth, and the broth evaluated for AFP as described previously. A portion of each colony is also streaked on "drop-out" plates to confirm any genetic markers (e.g., 2102-pSEY210-MT38-3 has leucine and histidine auxotrophies). Cells from colonies in which the genetic markers check out and which produce the highest levels of AFP are used to make the glycerol stock. The remaining portion of the desired colony is individually grown up in 1 liter of SCM-bases for 24 hours to a cell density of 40 to 50 million cells per ml. The cell suspensions are mixed with 500 ml of YPD (yeast extract, peptone, dextrose) containing 50% glycerol and aseptically aliquoted into sterile screw cap 10 ml/tubes for storage at −70° C.

Scale-up of AFP Fermentation—Flask Stage. A 10 ml AFP A(38) yeast inoculation stock culture prepared as described above, is removed from −70° C., thawed and the entire contents aseptically transferred to 250 ml of SCM-bases contained in a 1 liter baffled shake flask (¹⁄25 dilution). The flasks were incubated at 30° C. with shaking for 24 hours at which time the cell densities should be about 50 million per ml. This represents about six generations of growth.

Scale-up of AFP Fermentation—Carboy Stage. Two hundred ml from the flask stage is aseptically transferred to a 15 liter carboy containing 12 liters of sterile medium composed of yeast nitrogen base without amino acids and ammonium sulfate, but with histidine, leucine, glutamate, and aspartate at 40 mg/l and biotin at 0.1 mg/l, 2% glucose and 1% DifCo casamino acids. The medium in the carboy can be stirred by placing a large magnetic stirring bar into the carboy and the inoculated carboy is placed in an incubator atop a magnetic stir plate. Stirring via the magnetic stir bar is maintained at near maximum to keep the cells suspended. The carboy temperature is held at 28°–30° C. The lids on the carboys are kept loose to allow for gas exchange. After 24 hours incubation, the cell density should be 50 million cells per ml representing about six generations of growth.

Scale-up of AFP Fermentation-Seed Tank Stage. Twelve liters of inoculum from a single carboy is used to inoculate 250 liters of the same medium contained in a fermenter with approximately 300 liters capacity—the seed tank. The "seed tank" should be incubated at 28° C. with stirring. After 24 hours incubation, the cell density should be 50 million cells per ml with six generations of growth.

Scale-up of AFP Fermentation Production Tank Stage. The "seed tank" is aseptically transferred into the "production tank" which contains 1000 liter of medium identical to that above with the exception that it has 5% rather than 2% glucose, sterilized separately. Inoculum is added until the target inoculation rate of one to two million cells per ml is achieved. Samples are taken beginning at 22 hours after inoculation, processed by C18/dialysis, and analyzed for AFP. The presence of AFP at each step of the scale-up and in the production tanks is monitored by the "Cronan Thaw/Freeze" functionality test. AFP should be detected at each stage. When AFP yields peak in the production tank stage, routinely between 25 and 28 hours, the fermenter is rapidly cooled and harvested.

Pilot Scale Recovery of AFP. The yeast can be separated from the AFP-containing fermentation broth by centrifugation. The concentrate was further clarified by means of sheet filtration. The AFP can be recovered from the clarified fermentation broth as follows. The clarified broth is first subjected to an ultrafiltration step to remove large proteins such as proteases. A number of types of ultrafiltration membranes of various pore sizes can be used. For example, a UF2000 MXWCO (nominal molecular weight cut off) membrane was found to retain the majority of the broth proteins while passing 99% of the AFP. The AFP containing filtrate is then subjected to a second ultra-filtration step to concentrate the AFP (AFP retained). For example, a UF500 polysulphone MWCO membrane was found to retain about 95% of the AFP, resulting in a 300 fold concentration over the starting broth. The AFP containing concentrate is then purified by preparative RF-HPLC.

Purification of Yeast-Derived AFP A from UF500 concentrate. Yeast AFP A can be purified from a UF500 concentrate as follows. The UF500 concentrate can be pumped onto a preparative C4 RP-HPLC column and the bound AFP eluted with 60% water, 40% acetonitrile, and 0.1% TFA. The eluant is collected, the solvent and a portion of the water evaporated using a SpeedVac Concentrator and the aqueous concentrate from various runs pooled and frozen. The recombinant yeast—derived AFP A purified as described above is highly efficacious when functionality is assessed by the "sucrose ice crystal growth test."

The following example illustrates how AFP can be used in a frozen dessert to control ice crystal size and water migration, and thereby maintain product quality over an extended period, stored under abusive conditions. We envision that our AFPs (AFP A(38), AFP A(42), and AFP A(10)) will have many such uses in frozen foods. We also envision that our AFPs can be useful in protection of other items, such as organs to be transplanted, from ice crystal damage.

EXAMPLE 3

Current AFP Pilot Production

Although recombinant yeast-derived AFP has been produced at the 1,000 liter scale, due to several improvements in the process, similar quantities of AFP are currently being produced at the 10 liter scale. Previously, AFP broth yields were in the 1 mg/L range. Currently with refinements, functional AFP yields typically average about 70 mg/L and range from 50 to 90 mg/L. Overall recovery of functional AFP averages 50 mg/L. Briefly, the current process is described below.

Fermentation

Fermentations are carried out in a 12 L Wheaton Integral Proteus Fermentor System which is controlled by a Macintosh IIci computer. Many other similar fermentation systems could be used. Using this fermentor system, 10 liter fermentations of the batch mode are conducted. Each fermentation requires a specific duration of 11.5 hours (30° C.). At this time (EOF=11.5 hours) the automated fermentor pumps out 9.5 liters of the fermentation broth over a 30 minute interval, leaving 0.5 liters as inoculum to start the next fermentation. Within one minute of the fermented broth being removed, 9.5 liters of fresh sterile medium is pumped in over 30 minutes. Eleven and one half hours later, the process is repeated resulting in two fermentations per day. The fermentation duration is extremely important and longer times result in proteolytic degradation of AFP while shorter times result in much lower levels of AFP produced.

Of the above fermentation, the medium is a critical part. For a given strain of yeast, glucose, amino acids, and vitamin concentrations must be optimized. A good starting point for the medium ingredients are as follows: 2 to 10% glucose, 1 to 5% casamino acids, and 6.7 to 50 g/L Difco yeast nitrogen base. Once basic ranges are found for a given yeast strain, then single changes in each of the many individual ingredients can be determined.

Of the above fermentation, many yeast strains are suitable. In our case, the original AFP strain was a petite—an isolate of the original strain (non-petite) was obtained by plating on selective medium (yeast extract, peptone, and a non-fermentable carbon source such as acetate). The non-petite isolate of this strain was found to produce higher levels of AFP.

Processing of fermentation broth and recovery of AFP

At the end of fermentation (11.5 hour point) as described above, the fermentated broth is pumped from the fermentor and into a container held on ice. After an appropriate amount of material is obtained (20–50 liters), it is clarified (yeast removed) using a 2 micrometer ceramic crossflow filter. The AFP containing clarified permeate is then passed through a UF2000 ultrafiltration membrane to remove large proteins including proteases. The UF2000 permeate is then subjected to a UF300 ultrafiltration which retains the AFP and acts to concentrate it. The crude AFP can then be used as is, since it is fully functional in this form, or can be purified via HPLC.

EXAMPLE 4

Incorporation and Evaluation of Yeast-Derived AFP in Ice Cream

The effectiveness of extremely low levels of yeast-derived AFP A(38) in inhibiting ice crystal growth in ice cream was demonstrated in storage stability tests. Typically, a standard ice cream mix without stabilizers was prepared, divided into several portions, and AFP was added at various concentrations (control portions did not contain AFP). The samples were then evaluated as follows. Ice cream containing yeast-derived AFP A(38) and control samples were stored for several weeks in a Brazilian Ice Box cycled between 0° and 20° F. (12 hours at 20° and 12 hours at 20° F.), and observed for ice crystal growth using a cryo-scanning microscope. Little or no growth of ice crystals was observed in ice cream containing AFP at level of 0.00025% (2.5 ppm) or greater, while significant growth occurred in the control. The appearance of the abused AFP A(38)—containing ice cream was significantly better than the control, showing no evidence of surface ice formation. Tests have shown that the efficacy of AFP is greatly diminished at 0.0001%. The observations that the lower limit of a detectable effect of yeast-derived AFP A(38) is in the range of 0.0001% (1 ppm)—in water (as assessed by the ice crystal morphology test), 20% sucrose (as assessed by the "Cronan Thaw/Freeze" test), and in ice cream (as described above)—demonstrates that the efficacy of yeast-derived AFP A(38) is not significantly affected by the presence of other molecules (e.g., butter fats, milk proteins, flavoring, etc.) and broadens the arena of potential applicability in food and non-food systems.

Representatives of the yeast strains that can be used are *Saccharomyces cerevisiae* ATCC Nos. 42,752, 42,681 and 42,675. Other species of yeast may also be used with obvious and appropriate modifications of this invention. In general, any alpha strain of yeast can be used that has a Uracil 3–52 deletion.

Representative of the plasmids that can be used are those disclosed by Emr et al. in Proc. Natl. Acad. Sci. U.S.A., Vol. 80, pp. 7060–084, December 1983, which is incorporated by reference herein. Especially preferred is the plasmid pSEY210.

We claim:

1. An expression vector suitable for transformation into S. cerevisiae yeast so that upon such transformation the yeast expresses and secretes an antifreeze protein without a methionine at a N terminus of the protein, the vector comprising a DNA sequence encoding the protein having an amino acid sequence according to SEQ ID NO:1, except that one amino acid is replaced with a different amino acid in SEQ ID NO:1.

2. The vector of claim 1, wherein the amino acid sequence is according to SEQ ID NO:8.

3. The vector of claim 1, wherein the amino acid sequence is according to SEQ ID NO:10.

4. A S. cerevisiae yeast cell containing the vector of claim 1.

5. A method of producing an antifreeze protein comprising the steps of:
transforming the expression vector of claim 1 into a S. cerevisiae yeast culture to yield transformed yeast cells;
culturing the transformed yeast cells under suitable conditions for expression and secretion of a recoverable amount of antifreeze protein; and
recovering the secreted antifreeze protein by:
(a) passing the fermented broth through a filter medium sized to retain the yeast cells and wherein a first filter permeate is recovered;
(b) passing the first filter permeate through a first ultrafiltration membrane sized to retain proteins, other than the secreted antifreeze protein, larger than 2000 daltons and wherein a second filter permeate is recovered; and
(c) passing the second filter permeate through a second ultrafiltration membrane sized to retain proteins, including the secreted antifreeze protein, larger than 500 daltons and whereby the second ultrafiltration membrane acts to concentrate the secreted antifreeze protein.

6. A S. cerevisiae yeast cell containing the vector of claim 2.

7. A method of producing an antifreeze protein comprising the steps of:
transforming the expression vector of claim 2 into a S. cerevisiae yeast culture to yield transformed yeast cells;
culturing the transformed yeast cells under suitable conditions for expression and secretion of a recoverable amount of antifreeze protein; and recovering the secreted antifreeze protein by:
- (a) passing the fermented broth through a filter medium sized to retain the yeast cells and wherein a first filter permeate is recovered;
- (b) passing the first filter permeate through a first ultrafiltration membrane sized to retain proteins, other than the secreted antifreeze protein, larger than 2000 daltons and wherein a second filter permeate is recovered; and
- (c) passing the second filter permeate through a second ultrafiltration membrane sized to retain proteins, including the secreted antifreeze protein, larger than 500 daltons and whereby the second ultrafiltration membrane acts to concentrate the secreted antifreeze protein.

8. A *S. cerevisiae* yeast cell containing the vector of claim 3.

9. A method of producing an antifreeze protein comprising the steps of:

transforming the expression vector of claim 3 into a *S. cerevisiae* yeast culture to yield transformed yeast cells;

culturing the transformed yeast cells under suitable condition for expression and secretion of a recoverable amount of antifreeze protein; and recovering the secreted antifreeze protein by:
- (a) passing the fermented broth through a filter medium sized to retain the yeast cells and wherein a first filter permeate is recovered;
- (b) passing the first filter permeate through a first ultrafiltration membrane sized to retain proteins, other than the secreted antifreeze protein, larger than 2000 daltons and wherein a second filter permeate is recovered; and
- (c) passing the second filter permeate through a second ultrafiltration membrane sized to retain proteins, including the secreted antifreeze protein, larger than 500 daltons and whereby the second ultrafiltration membrane acts to concentrate the secreted antifreeze protein.

* * * * *

UNITED STATES PATENT AND TRADEMARK OFFICE
CERTIFICATE OF CORRECTION

PATENT NO. : 5,849,537
DATED : December 15, 1998
INVENTOR(S) : Matthew L. Tripp, et al.

It is certified that error appears in the above-indentified patent and that said Letters Patent is hereby corrected as shown below:

At Column 1, Line 26: Insert --.-- after "freezing"

At Column 3, Line 16: Insert --.-- after "respectively"

At Column 3, Line 38: Insert --.-- after "FIGS. 5a-5d"

At Column 5, Line 39: Insert --.-- after "ingredient"

At Column 6, Line 58: Delete "Fig. 5", insert --Figs. 5a-5d--.

At Column 9, Line 4: Insert --.-- after "transformants"

At Column 13, Line 4: Insert --.-- after "previously"

At Column 14, before Line 33: Insert --The one letter amino acid codes are D=ASP; E=GLU; A=ALA; S=SER; K=LYS; L=LEU; N=ASN; T=THR; R=ARG; V=VAL.--

At Column 17, Line 6: Delete second instance of "20°", insert --0°--

Signed and Sealed this

Twenty-third Day of November, 1999

Attest:

Attesting Officer

Q. TODD DICKINSON

Acting Commissioner of Patents and Trademarks

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 37 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
        ( A ) ORGANISM: Pseudopleuronectus americanus ( x i ) SEQUENCE DESCRIPTION: SEQ ID NO:1:

```
Asp Thr Ala Ser Asp Ala Ala Ala Ala Ala Ala Leu Thr Ala Ala Asn
 1               5                  10                      15

Ala Lys Ala Ala Ala Glu Leu Thr Ala Ala Asn Ala Ala Ala Ala Ala
            20                  25                  30

Ala Ala Thr Ala Arg
        35
```

( 2 ) INFORMATION FOR SEQ ID NO:2:

( i ) SEQUENCE CHARACTERISTICS:
        ( A ) LENGTH: 1095 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Pseudopleuronectus americanus ( x i ) SEQUENCE DESCRIPTION: SEQ ID NO:2:

```
GCACA ACACTGGGGG AGTGTTGTAC CAATCTGCTC AGATTGGTCG ACAGTCAAGC        55
```

-continued

| | | | | | |
|---|---|---|---|---|---|
| GATGACCCAG | GCTCCAGTTA | CTATAAAACA | GATTCACATT | GACCTGGATA | TTCACCACAT | 115 |
| CTTCATTTTG | TAGTGAACCA | GTGCTCCCTA | CAAGTTCTCA | AAATGGCTCT | CTCACTTTTC | 175 |
| ACTGTCGGAC | AATTGATTTT | CTTATTTTGG | ACAATGAGGT | ACGTGAACAC | TCACTTTGTT | 235 |
| TCTTCTATGA | ATCTGGTTTT | ACTGTAAATA | TCTTGGAAGG | AAGGAAGGAT | ATCTGCATTA | 295 |
| TCCCCGAGGG | GCCATTTGTT | TTACAGCCAG | CGGTGAAAGA | TGAAGATCTT | CATCCGTGTT | 355 |
| CATCTGTTTG | ACCCTGATTA | ACACAAGATG | GTCACATGGA | CCATCTTTAT | TTACATAATG | 415 |
| TTTCATCAGC | ACTTCCTGTT | TTCAGCCCGA | AACTTAAAGA | GGCCTCATGG | AAACTTCCTG | 475 |
| ATGATCTGGT | GACACCTGCT | GGTTGAAGGA | AACAGAGTTT | GAGAGGCGGA | AGAAAAAATT | 535 |
| ATTTTAGTTT | GAATGAAGAA | GCTGTCATTT | GATTTCATGT | TGGGGGGGGG | GGGGTCATC | 595 |
| ACACACAGAT | ATTGATAACT | GTCATCACTG | AGTTTGGTGA | AAGTGACGGA | CCAGTAAATG | 655 |
| TTGTGATATA | TAATATTATC | ATAATAATTA | TAATAATACC | ATTAATCTCT | GCAGAATCAC | 715 |
| TGAAGCCAGA | CCCGACCCCG | CAGCCAAAGC | CGCCCCAGCA | GCAGCTGCCG | CCCCTGCCGC | 775 |
| AGCCGCCCCA | GACACCGCCT | CTGACGCCGC | CGCTGCAGCC | GCCCTTACCG | CCGCCAACGC | 835 |
| CAAAGCCGCT | GCCGAACTCA | CTGCCGCCAA | CGCCGCCGCC | GCCGCAGCAG | CCACCGCCAG | 895 |
| AGGTTAAGGA | TCGTGGTCGT | CTTGATGTGG | GATCATGTGA | ACATCTGAGG | AGCGAGATGT | 955 |
| TACCAATCTG | CTGAATAAAC | CTGAGAAGCT | GATTGTTAAA | AACCAAGTGT | CCTGTTCATT | 1015 |
| TCATCTCTGA | AAGTCCGTCA | CAGTTTCTGT | AGATCATGTA | GACTCCAGGA | AGTGATGCCA | 1075 |
| TTGTGCTGTT | GAACCTGCAG | | | | | 1095 |

(2) INFORMATION FOR SEQ ID NO:3:

(i) SEQUENCE CHARACTERISTICS:
        (A) LENGTH: 146 base pairs
        (B) TYPE: nucleic acid
        (C) STRANDEDNESS: double
        (D) TOPOLOGY: linear (ii) MOLECULE TYPE: Other Nucleic Acid (iii) HYPOTHETICAL: YES (iv) ANTI-SENSE: NO (xi) SEQUENCE DESCRIPTION: SEQ ID NO:3:

| | | | | | |
|---|---|---|---|---|---|
| AGCTT | CTTTGGATAA | AAGAGACACT | GCTTCTGACG | CTGCCGCTGC | TGCTGCTTTG | 55 |
| ACTGCCGCTA | ACGCTAAGGC | CGCTGCTGAA | TTGACTGCTG | CTAACGCTGC | CGCCGCCGCC | 115 |
| GCTGCCACTG | TTAGATAAGG | ATCCGAATTC | G | | | 146 |

(2) INFORMATION FOR SEQ ID NO:4:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: YES (xi) SEQUENCE DESCRIPTION: SEQ ID NO:4:

| | | | | | |
|---|---|---|---|---|---|
| AGCTT | CTTTGGATAA | AAGAGACACT | GCTTCTGACG | CTGCCGCTGC | TGCTGCTTTG | 55 |
| ACTGCCGCTA | CCGC | | | | | 69 |

(2) INFORMATION FOR SEQ ID NO:5:

( i ) SEQUENCE CHARACTERISTICS:
    ( A ) LENGTH: 77 base pairs
    ( B ) TYPE: nucleic acid
    ( C ) STRANDEDNESS: single
    ( D ) TOPOLOGY: linear ( i i ) MOLECULE TYPE: Oligonucleotide ( i i i ) HYPOTHETICAL: YES ( x i ) SEQUENCE DESCRIPTION: SEQ ID NO:5:

```
TAAGG CCGCTGCTGA ATTGACTGCT GCTAACGCTG CCGCCGCCGC CGCTGCCACT        55
GCTAGATAAG GATCCGAATT CG                                            77
```

( 2 ) INFORMATION FOR SEQ ID NO:6:

( i ) SEQUENCE CHARACTERISTICS:
        ( A ) LENGTH: 68 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: YES ( x i ) SEQUENCE DESCRIPTION: SEQ ID NO:6:

```
AGAAA CCTATTTTCT CTGTGACGAA GACTGCGACG GCGACGACGA CGAAACTGAC        55
GGCGATTGCG ATT                                                      68
```

( 2 ) INFORMATION FOR SEQ ID NO:7:

( i ) SEQUENCE CHARACTERISTICS:
        ( A ) LENGTH: 78 base pairs
        ( B ) TYPE: nucleic acid
        ( C ) STRANDEDNESS: single
        ( D ) TOPOLOGY: linear ( i i ) MOLECULE TYPE: Oligonucleotide ( x i ) SEQUENCE DESCRIPTION: SEQ ID NO:7:

```
CCGGC GACGACTTAA CTGACGACGA TTGCGACGGC GGCGGCGGCG ACGGTGACGA        55
TCTATTCCTA GGCTTAAGCA GCT                                           78
```

( 2 ) INFORMATION FOR SEQ ID NO:8:

( i ) SEQUENCE CHARACTERISTICS:
        ( A ) LENGTH: 37 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:8:

```
Asp Thr Ala Ser Asp Ala Ala Ala Ala Ala Leu Thr Ala Ala Asn
 1               5                  10                  15
Ala Lys Ala Ala Ala Glu Asn Thr Ala Asn Ala Ala Ala Ala
             20                  25                  30
Ala Ala Thr Ala Arg
         35
```

(2) INFORMATION FOR SEQ ID NO:9:

(i) SEQUENCE CHARACTERISTICS:
(A) LENGTH: 37 amino acids
(B) TYPE: amino acid
(C) STRANDEDNESS: single
(D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:9:

```
Asp Thr Ala Ser Asp Ala Ala Ala Ala Ala Ala Leu Thr Ala Ala Asn
1               5                   10                  15
Ala Lys Ala Ala Ala Glu Leu Thr Ala Ala Asn Ala Ala Ala Ala Ala
                20              25                  30
Ala Ala Thr Val Arg
        35
```

(2) INFORMATION FOR SEQ ID NO:10:

(i) SEQUENCE CHARACTERISTICS:
(A) LENGTH: 37 amino acids
(B) TYPE: amino acid
(C) STRANDEDNESS: single
(D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:10:

```
Asp Thr Ala Ser Asp Ala Ala Ala Ala Ala Thr Leu Thr Ala Ala Asn
1               5                   10                  15
Ala Lys Ala Ala Ala Glu Leu Thr Ala Ala Asn Ala Ala Ala Ala Ala
                20              25                  30
Ala Ala Thr Ala Arg
        35
```